United States Patent [19]

Bino et al.

[11] Patent Number: 4,832,877

[45] Date of Patent: May 23, 1989

[54] TETRANUCLEAR SULFIDO-BRIDGED COMPLEX OF CR(III) HAVING A STRONGLY MAGNETIC GROUND STATE

[75] Inventors: Avi Bino, Jerusalem, Israel; David C. Johnston, Whitehouse Station; Edward I. Stiefel, Bridgewater, both of N.J.

[73] Assignee: Exxon Research and Engineering Company, Florham Park, N.J.

[21] Appl. No.: 101,674

[22] Filed: Sep. 28, 1987

[51] Int. Cl.[4] .......................... C11C 1/00; C07F 11/00
[52] U.S. Cl. ...................................... 260/414; 556/61; 556/63; 556/7; 556/31; 556/58
[58] Field of Search .................... 260/414; 556/61, 63, 556/7, 31, 58

[56] References Cited

PUBLICATIONS

I. L. Eremenko et al, "Interaction of Heteronuclear Chromium-Containing Clusters . . . ", Inorg. Chim. Acta. 73 (1983), 225–229.

Primary Examiner—Patrick P. Garvin
Assistant Examiner—E. D. Irzinski
Attorney, Agent, or Firm—Joseph J. Dvorak

[57] ABSTRACT

Broadly stated, the present invention encompasses tetranuclear sulfide-bridged complexes of Cr(III) having bridging organo-carboxylate ligands. Indeed, in one embodiment, the present invention is directed toward a novel composition of matter having a complex cation of the general formula $Cr_4S(RCO_2)_8(L)_4{}^{2+}$, wherein R represents alkyl groups having from 1 to 12 carbon atoms, L represents a ligand or ligands containing a donor atom selected from oxygen, nitrogen, carbon, and sulfur. In the complex of the present invention, the four Cr(III) atoms are bound to a central tetrahedral sulfur atom. The chromium atoms also are octahedrally coordinated with bridging carboxylates and the ligand molecule. Also, the bridging carboxylates, $RCO_2^-$ of the above formula, are the same or different carboxylates.

17 Claims, 1 Drawing Sheet

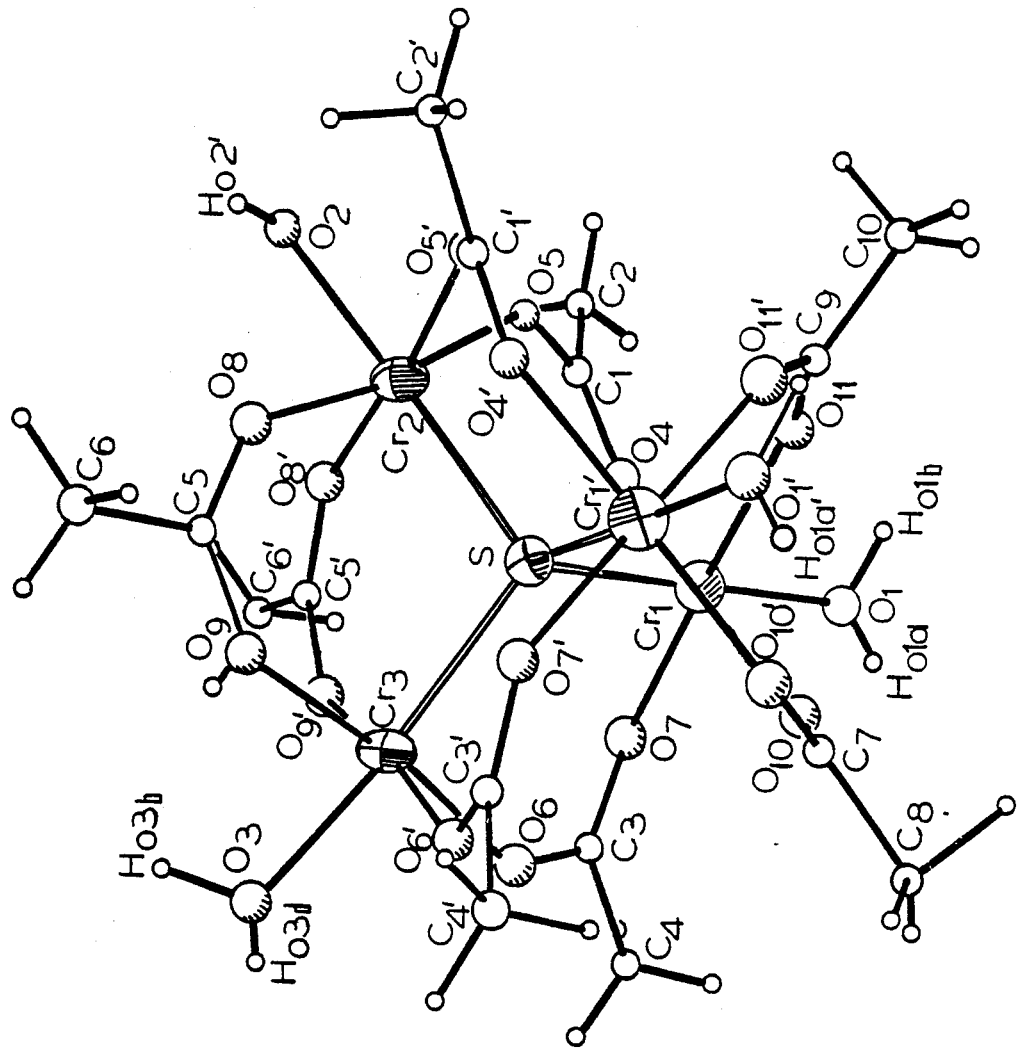

TETRANUCLEAR SULFIDO-BRIDGED COMPLEX OF CR(III) HAVING A STRONGLY MAGNETIC GROUND STATE

FIELD OF THE INVENTION

This invention relates to novel compositions containing chromium and sulfur. More specifically, this invention relates to novel tetranuclear sulfido-bridged complexes of Cr (III) having strongly magnetic ground states and methods of making the same.

BACKGROUND OF THE INVENTION

Various complexes containing two, three and four chromium atoms are known. With respect to bi- and trinuclear chromium complexes, see, for example, *Magneto-Structural Correlation in Exchange Coupled Systems*, Willett et al., Ridel, Dordrecht, pp. 497–522 (1985). See also Dubicki et al., *Inorganic Chemistry*, 11, 1869 (1972) and Figgis et al., *Nature* (London), 205, 694 (1964) who report a trinuclear chromium (III) acetate in which the three chromium atoms are linked to a central oxygen atom.

Two complexes of chromium that have four chromium atoms bound to a central sulfur atom have been reported in journal articles. For instance, Darensburg et al., *Organometallics*, 3, 1598–1600 (1984) report the synthesis of a sulfur-capped trinuclear chromium carbonyl cluster, $S[Cr(CO)_4]_3^{2-}$; and Hoefler et al., *J. Am. Chem. Soc.*, 105, 6338–6339 (1983) report the synthesis of $[PPN]_2(\mu_2-CO)_3(CO)_9Cr_3(\mu_4-S)Cr(CO)_5]$, in which the anion consists of chromium triangle capped with an $SCr(CO)_5$ group.

Chromium complexes with bridging ligands formed from benzoic acid and containing three chromium atoms connected to a central sulfur atom have been reported by Eremenko et al., *Inorg. Chim. Acta*, 73, 225–229 (1983).

None of these references disclose a tetranuclear sulfide bridged complex of Cr (III). Accordingly, the invention embodied herein is believed by the applicants to be novel in all its aspects.

SUMMARY OF THE INVENTION

Broadly stated, the present invention encompasses tetranuclear sulfide-bridged complexes of Cr(III) having bridging organo-carboxylate ligands. Indeed, in one embodiment, the present invention is directed toward a novel composition of matter having a complex cation of the general formula $Cr_4S(RCO_2)_8(L)_4^{2+}$, wherein R represents alkyl groups having from 1 to 12 carbon atoms, L represents a ligand or ligands containing a donor atom selected from oxyen, nitrogen, carbon, and sulfur. In the complex of the present invention, the four Cr(III) atoms are bound to a central tetrahedral sulfur atom. The chromium atoms also are octahedrally coordinated with bridging carboxylates and the ligand molecule. Also, the bridging carboxylates, $RCO_2$ of the above formula, are the same or different carboxylates.

The compositions of the present invention are especially unique in that they have ferromagnetic properties. As as a result thereof, these compositions are particularly useful as contrasting agents for nuclear magnetic resonance (NMR) imaging, shiftless relaxation reagents to aid the accumulation of $^{13}C$ NMR data, orienting agents for attached polymers in a magnetic field, selective microwave absorbers for localized heating of a particular organelle, organ, organism or inanimate substructure, or as part of a thermometer for use above 0.2 degrees Kelvin.

The novel compositions disclosed are made by reacting a source of chromium, such as chromium metal or chromium carbonyl with sulfur and the appropriate source of coordinating bridging carboxylate, such as the corresponding carboxylic acid, acid anhydride or mixtures thereof at temperatures and for time sufficient to form the composition.

The invention will now be illustrated in non-limiting fashion by the following example and discussion.

BRIEF DESCRIPTION OF THE DRAWING

The DRAWING is a depiction of the structure of a complex cation of the present invention.

DETAILED DESCRIPTION OF THE PREFERRED EMBODIMENTS

The invention encompasses tetranuclear sulfide-bridged complexes of Cr(III) including bridging ligands from carboxylates. Indeed, the complex cations of the present invention are represented by the general formula $Cr_4S(RCO_2)_8(L)_4^{2+}$, wherein R is an alkyl group having from 1 to 12 carbon atoms and L is a ligand containing a donor atom selected from oxygen, nitrogen, carbon, and sulfur. Preferably R is methyl and L is selected from $H_2O$, $CH_3CN$ and $CH_3OH$.

It should be noted that the bridging carboxylates in the above formula are preferably all of the same type; however, such is not necessary and a mixture of different bridging carboxylates may be employed, if so desired.

Compounds containing the novel complex cation will contain an anion. Any anion which will render the compound stable is suitable. Examples of such anions are $BF_4^-$, $NO_3^-$, $B(C_6H_5)_4^-$, $SO_4^{2-}$, $MoO_4^{2-}$, $Cl^-$, $Br^-$, and the like.

These complexes are made by reacting $Cr(CO)_6$ or chromium metal with sulfur and an appropriate source of bridging organo-carboxylates such as organo-carboxylic acid and organo-carboxylic anhydrides at a temperature and for a time sufficient to form the complex cation. The reaction may be conducted in an inert solvent; however, when the source of the bridging carboxylate is a liquid a solvent is not necessary. Indeed, it is particularly preferred to react the $Cr(CO)_6$ or chromium metal with sulfur and with a mixture of an acid and an anhydride. For example, especially preferred is a one-to-one mixture of acetic acid and acetic anhydride. The reaction also is preferably conducted at elevated temperatures such as the refluxing temperature of that of the source of coordinating bridging carboxylate.

The reaction does yield a mixture of cationic species which can be separated by generally known techniques. For example, these species are separable by ion-exchange chromatography. Moreover, elution with an appropriate source of anion will yield the complex cation in a form which can be crystallized as a salt by slow evaporation of the solvent, by recrystallization from a suitable solvent, and the like.

The following is an example of one species of the present invention and its method of preparation.

EXAMPLE $Cr_4S(O_2CCH_3)_8(H_2O)_4[(BF_4)_2\cdot H_2O]$ was prepared by adding $Cr(CO)_6$ (2 grams, 9.1 millimoles) and elemental sulfur (0.3 grams, 9.4 millimoles) to 50 ml of a one-to-one mixture of acetic acid/acetic anhydride and refluxing the mixture for 2.5 hours. The reaction mixture then was diluted with 100 ml $H_2O$ and adsorbed on an ion-exchange column containing Dowex 50W-X2, a cation exchange resin containing sulfonated polystyrene sold by Dow Chemical Company, Midland, Michigan. Elution with 0.1 M $HBF_4$ solution removed a green band of $[Cr_3O(O_2CCH_3)_6(H_2O)_3]^+$. The blue band of $[Cr_4S(O_2CCH_3)_8(H_2O)_4]^{2+}$ was removed with 0.5 M $HBF_4$ solution and the blue solution was placed in a dessicator for evaporation of the water. Upon evaporation of the water, dark blue crystals were obtained. These were recrystallized from methanol by slowly evaporating that solvent. Elemental analysis was as follows: Calculated for $[Cr_4S(O_2CCH_3)_8(H_2O)_4(BF_4)_2 \cdot H_2O$; C, 19.67; H, 3.48; S, 3.28; Cr, 21.31; F, 15.57. Found: C, 18.93; H, 3.46; S, 3.50; Cr, 20.48; F, 15.39.

The compound also was analyzed by single crystal X-ray diffraction analysis techniques. The key parameters for determining the structure of the complex obtained in accordance with the present invention is shown in Table I.

TABLE I

| Parameters from Structure Determination of $[Cr_4S(O_2CCH_3)_8(H_2O)_4](BF_4)_2 \cdot H_2O$ | |
| --- | --- |
| a, Å | 21.066(4) |
| b, Å | 19.086(3) |
| c, Å | 9.323 |
| α, deg | 90.0 |
| β, deg | 90.0 |
| α, deg | 90.0 |
| V, Å$^3$ | 3,748(1) |
| z | 4.0 |
| Calculated Density, g/cm$^3$ | 1.73 |
| Reflections with F > 3σ | 2,939.0 |
| μ, cm$^{-1}$ | 1.27 mn$^{-1}$ |
| sinθ/λ (max) | 0.650 |
| R | 0.048 |
| $R_w$ | 0.049 |
| GOF | 2.03 |

Atomic coordinates for non-hydrogen atoms are given in Table II.

TABLE II

Atomic Coordinates for Non-Hydrogen Atoms in Crystalline $[Cr_4S(O_2CCH_3)_8(OH_2)_4](BF_4)_2 \cdot H_2O^a$

| Atom Type$^b$ | Fractional Coordinates | | | Equivalent Isotropic Thermal Parameter B, Å$^2$ × 10$^c$ |
| --- | --- | --- | --- | --- |
| | 10$^4$x | 10$^4$y | 10$^4$z | |
| Cation | | | | |
| Cr$_1$ | 5,971(1) | 3,473(1) | 4,120(1) | 25(1) |
| Cr$_2$ | 4,414(1) | 2,500$^d$ | 5,078(1) | 21(1) |
| Cr$_3$ | 4,936(1) | 2,500$^d$ | 1,266(1) | 24(1) |
| S | 5,326(1) | 2,500$^d$ | 3,628(2) | 19(1) |
| O$_1$ | 6,539(2) | 4,300(2) | 4,614(4) | 44(1) |
| O$_2$ | 3,609(4) | 2,500$^d$ | 6,279(7) | 40(2) |
| O$_3$ | 4,518(4) | 2,500$^d$ | −692(6) | 42(2) |
| O$_4$ | 5,300(2) | 3,983(1) | 5,142(4) | 35(1) |
| O$_5$ | 4,737(2) | 3,208(2) | 6,412(3) | 32(1) |
| O$_6$ | 5,540(1) | 3,208(2) | 570(3) | 32(1) |
| O$_7$ | 5,732(2) | 3,962(1) | 2,361(3) | 31(1) |
| O$_8$ | 4,018(1) | 1,751(2) | 3,979(3) | 33(1) |
| O$_9$ | 4,341(1) | 1,739(2) | 1,969(3) | 34(1) |
| O$_{10}$ | 6,681(2) | 3,087(2) | 3,036(4) | 37(1) |
| O$_{11}$ | 6,253(2) | 3,087(2) | 5,944(3) | 36(1) |
| C$_1$ | 4,939(2) | 3,826(2) | 6,144(5) | 31(1) |
| C$_2$ | 4,712(3) | 4,395(3) | 7,114(7) | 60(2) |
| C$_3$ | 5,743(2) | 3,786(2) | 1,063(5) | 31(1) |
| C$_4$ | 6,015(4) | 4,288(3) | 1(6) | 61(2) |
| C$_5$ | 4,032(2) | 1,504(2) | 2,727(5) | 29(1) |
| C$_6$ | 3,627(3) | 871(3) | 2,473(7) | 29(1) |
| C$_7$ | 6,896(3) | 2,500$^d$ | 2,649(7) | 33(2) |
| C$_8$ | 7,463(4) | 2,500$^d$ | 1,688(13) | 54(3) |
| C$_9$ | 6,345(3) | 2,500$^d$ | 6,530(7) | 26(2) |
| C$_{10}$ | 6,572(4) | 2,500$^d$ | 8,038(9) | 41(2) |
| Anion | | | | |
| B | 7,752(4) | 4,190(4) | 7,532(10) | 64(3) |
| F$_1$ | 7,145(2) | 4,297(3) | 7,305(6) | 103(2) |
| F$_2$ | 8,068(3) | 4,779(3) | 7,627(6) | 127(2) |
| F$_3$ | 7,880(3) | 3,714(3) | 8,436(7) | 146(2) |
| F$_4$ | 7,926(4) | 3,922(4) | 6,203(7) | 195(4) |
| Water of Crystallization | | | | |
| O$_w$ | 3,212(4) | 2,500$^d$ | −314(8) | 92(3) |

$^a$The numbers in parentheses are the estimated standard deviations in the last significant digit.
$^b$Atoms are labeled in agreement with the drawing.
$^c$This is one-third of the trace of the orthogonalized B$_{ij}$ tensor.
$^d$This is a symmetry-required value and is therefore listed without an estimated standard deviation.

As is shown in the drawing, the complex cation of this invention consists of a central four coordinate sulfur atom bound to four chromium atoms which are in an approximate tetrahedral array. The chromium-chromium distances average 3.83 Å (range 3.72–3.91 Å). Each chromium atom is six-coordinated with a near-octahedral arrangement of five oxygen donors in the central sulfur atom. The one water ligand on each chromium lies trans to the sulfur atom. The remaining oxygen ligands of each chromium come from bridging acetate ligands. These are of two types: four acetate ligands are involved as two pairs of double bisses. These acetates are equivalent and related by an approximate S$_4$ axis. The overall symmetry of the cation is close to a D$_{2d}$ while that of inner Cr$_4$S core is very close to T$_d$.

The structure shown is related to that of beryllium basic acetate, Be$_4$O(CH$_3$CO$_2$)$_6$ (see Charalombous et al., Inorg. Chim. Acta, 14, [1975]), although in this structure, the Be atoms are tetrahedrally four-coordinated rather than octahedrally six-coordinated, as are the Cr atoms in the chromium complex.

Clearly, the complex of the present invention represents a new structural type containing a central four-coordinated sulfur atom, and four octahedral metal ions on the tetrahedral periphery. In addition to the unique structure of the complex of the present invention, it displays unusual magnetic behavior.

The magnetic susceptibility χ versus temperature T was measured on polycrystalline samples from 13° mK to 300° K. in magnetic fields, H, of 75 Gauss to 6.3 k Gauss using SQUID, Faraday and vibrating sample magnetometers (VSM). In addition, magnetization versus H isotherms were measured at 1.3° K. and 4.2° K. using the VSM. These data prove that the ground state of the Cr$_4$ cluster has a spin S=6, with a Landég factor g=2.00±0.02. Electron spin resonance data at 15° K. for the Cr complex frozen in solution yielded a very similar g value.

The chromium compound of the present invention is useful, for example, as a thermometer at temperatures above 0.2° K. By measuring the magnetic susceptibility, χ, of the compound, the temperature can be determined from the following relationship:

$$\chi = \chi_o + \frac{Ng^2\mu_B^2}{3Zk_BT} \sum_{S=0}^{6} G_s S(S+1)(2S+1) e^{-E_s/k_BT},$$

where $\chi_o = -4.66 \times 10^{-4}$ cm$^3$/mole Cr$_4$, $E = -JS(S+1)$ with $J/k_B = 14.5°$ K., $G_s = 4, 9, 11, 10, 6, 3$ and $1$ for $S = 0, 1, \ldots, 6$, respectively, N is Avogadro's number, $g = 2.00$ is the Landég-factor, $\mu_B$ is the Bohr magnetron, $k_B$ is Boltzmann's constant, and Z is the partition function:

$$Z = \sum_{S=0}^{6} G_s(2S+1) e^{-E_s/k_BT}$$

It should be understood that the foregoing disclosure, description and example are only illustrative of the invention. Various changes to the details of the invention will be apparent to the skilled worker, and may be made within the scope of the appended claims without departing from the spirit of the invention.

What is claimed is:

1. A compound containing a complex cation having a central four coordinate sulfur atom bound to four chromium atoms which are substantially in a tetrahedral array and which have bridging organo-carboxylate ligands, and said compound containing an anion capable of rendering the compound stable.

2. The compound of claim 1 wherein the chromium atoms are octahedrally coordinated with the brigding carboxylate ligands.

3. The compound of claim 1 wherein the anions of selected from BF$_4^-$, NO$_3^-$, B(C$_6$H$_5$)$_4^-$, SO$_4^{2-}$, MoO$_4^{2-}$, Cl$^-$ and Br$^-$.

4. A compound containing a cation having the formula:

Cr$_4$S(RCO$_2$)$_8$(L)$_4^{2+}$ wherein R is an alkyl group having from 1 to 12 carbon atoms; L is a ligand or ligands containing a donor atom selected from oxygen, nitrogen, carbon, and sulfur; and an anion capable of rendering the cation stable.

5. The compound of claim 4 wherein RCO$_2$ groups represent the same organo-carboxylate.

6. The compound of claim 4 wherein the RCO$_2$ groups represent a mixture of organo-carboxylates.

7. The compound of claim 5 wherein R is methyl.

8. The compound of claim 4 wherein L is selected from H$_2$O, CH$_3$OH, and CH$_3$CN.

9. The compound of claim 7 wherein L is H$_2$O.

10. The compound of claim 7 or 9 including an anion selected from the group consisting of BF$_4^-$, NO$_3^-$, B(C$_6$H$_5$)$_4^-$, SO$_4^{2-}$, MoO$_4^{2-}$, Cl$^-$ and Br$^-$.

11. The compound of claim 10 wherein the anion is selected from the group consisting of BF$_4^-$.

12. A method of forming a compound containing a tetranuclear sulfur-bridged complex of Cr(III) having bridging organo-carboxylate comprising: reacting zero valent chromium and sulfur with a source of the organo-carboxylate at temperatures and for a time sufficient to form said compound containing said complex.

13. The method of claim 12 wherein said chromium is present as chromium hexacarbonyl.

14. The method of claim 13 wherein said source of carboxylate is selected from the group consisting of organo-carboxylic acids, acid anhydrides and mixtures thereof.

15. The method of claim 14 wherein said source of carboxylate is a mixture of carboxylic acid and its corresponding acid anhydride.

16. The method of claim 15 wherein said carboxylic acid is acetic acid and said acid anhydride is acetic anhydride.

17. The method of claim 15 wherein said temperature is the reflux temperature of said mixture of acetic acid and acetic anhydride.

* * * * *